(12) United States Patent
McDaniel

(10) Patent No.: US 9,538,759 B2
(45) Date of Patent: Jan. 10, 2017

(54) CHEMICAL COMPOSITIONS AND METHODOLOGY TO ENHANCE PLANT GROWTH AND DEVELOPMENT

(71) Applicant: Robert Gene McDaniel, Tucson, AZ (US)

(72) Inventor: Robert Gene McDaniel, Tucson, AZ (US)

( * ) Notice: Subject to any disclaimer, the term of this patent is extended or adjusted under 35 U.S.C. 154(b) by 205 days.

(21) Appl. No.: 13/953,907

(22) Filed: Jul. 30, 2013

(65) Prior Publication Data

US 2015/0038330 A1     Feb. 5, 2015

(51) Int. Cl.
| | |
|---|---|
| *A01N 57/16* | (2006.01) |
| *A01N 37/40* | (2006.01) |
| *A01N 59/06* | (2006.01) |
| *A01N 25/00* | (2006.01) |

(52) U.S. Cl.
CPC .............. *A01N 57/16* (2013.01); *A01N 25/00* (2013.01); *A01N 37/40* (2013.01); *A01N 59/06* (2013.01)

(58) Field of Classification Search
CPC ......... A01N 57/16; A01N 37/40; A01N 59/06
See application file for complete search history.

(56) References Cited

U.S. PATENT DOCUMENTS

| 4,209,316 A * | 6/1980 | McDaniel et al. ............ 504/196 |
| 4,531,963 A * | 7/1985 | Wallach ........................ 504/289 |
| 2008/0092255 A1* | 4/2008 | Edgerton et al. ............ 800/289 |

OTHER PUBLICATIONS

David J. Parrish and A. Carl Leopold, "Confounding of Alternate Respiration by Lipoxygenase Activity", Plant Physiology (1978), 62, 470-472.*
Carolyn A. Brooks, Kenneth S. Yu and Cary A. Mitchell, "Salicylhydroxamic Acid Potentiates Germination of 'Waldmann's Green' Lettuce Seed", Plant Physiology (1985), 79, 386-388.*

* cited by examiner

*Primary Examiner* — John Pak
*Assistant Examiner* — Nathan W Schlientz
(74) *Attorney, Agent, or Firm* — Garrett James O'Sullivan

(57) ABSTRACT

Plant seeds, seedlings, or developing plants are treated with aqueous, dry, or appropriately solvated chemical formulations composed of nucleotides or nucleosides buffered with an effective amount of non-toxic biologically compatible agents, simultaneously with an antioxidant and lipoxygenase enzyme inhibitor. The purpose is to improve or optimize seed germination rate, seedling vigor, and ultimately plant growth characteristics and yield performance. In the preferred embodiment, seeds or other plant tissues are treated with adenosine monophosphate buffered with an excess amount of phosphoric acid salts at about pH 7.0 as described in U.S. Pat. No. 4,209,316. The improvement described in this application comprises the simultaneous addition of a similar quantity of propyl gallate to the adenosine monophosphate maintaining pH around 7.0 or below. Addition of a lesser, fractional quantity of a magnesium salt, such as magnesium sulfate, is to be included in the formulation to potentiate the action of the chemical treatment if planting soil or medium is shown to be magnesium deficient.

8 Claims, No Drawings

CHEMICAL COMPOSITIONS AND METHODOLOGY TO ENHANCE PLANT GROWTH AND DEVELOPMENT

REFERENCES CITED

| U.S. patent documents | | |
|---|---|---|
| 4,209,316 | June 1980 | McDaniel, et al. |
| 4,531,963 | July 1985 | Wallach |
| 4,925,477 | May 1990 | McDaniel |

OTHER PUBLICATIONS

Brooks, et al.,"Salicylhydroxamic Acid Potentiates Germination, etc." (1985), Plant Physiol., 79:386-388. (1985).

Goldstein, et al., "Cyanide-insensitive and Cyanide-insensitive O2 etc." (1979), Plant Physiol. 66:488-493. (1980).

Hajika, et al. "Induction of a Soybean, etc." (1994), JARQ 29, 73-76. (1995).

Ismail, et al. "Respiratory Rates and Alternative Pathway, etc." (1988), Crop Science, 29,976-980. (1989).

Leopold, et al., "Respiratory Pathways in Aged Soybean Seeds." Physiol. Plant., 49, 49-54. (1980).

Murashige, et al.,"A Revised Medium for Rapid Growth, etc." Physiol. Plant., 15, 473-497. (1962).

Musgrove, et al., "Is Male Sterility in Plants Related to, etc.," (1985), Plant Sci. 44, 7-11, (1986).

McDaniel, "The Physiology of Temperature Effects, etc." In: Breeding Plants for Less Favorable Environments. ed. Christiansen, J. Wiley and Sons, pp 13-45. (1982).

McDaniel, "Biochemical and Physiological Basis, etc." CRC Critical Reviews in Plant Sciences, 4, 227-246. (1986).

McDaniel, et al., "Water Stress and Carbon Isotope Discrimination, etc." Proceed. Beltwide Cotton Conf. 3, 1297-1300. (1994).

Parrish, et al., "Confounding of Alternate Respiration, etc." (1977) Plant Physiol. 62, 470-472, (1978).

Pfeiffer, et al., "Agronomic Performance of Soybean Lipoxygenase, etc." (1991) Crop Sci., 32, 357-362, (1992).

Smith, et al., "State-wide Survey in Arizona Shows Alfalfa Deficient in P and Mg." (1981) U. of Arizona Pl. Sci. Seminar Series, March, 2pp. (1981).

BACKGROUND OF THE INVENTION

Although recent advances in seed physiology and biochemistry, as well as increasing applications of genetic engineering techniques to plant breeding, have resulted in marked improvements in crop seed quality and field performance of planting seed, much remains to be accomplished to insure the most consistent performance of seed. Many problems involved in finding methods to insure the most consistent and uniform germination and seedling vigor remain to be solved. The present invention has the goal of improving planting seed germination and seedling vigor across an array of unfavorable planting environments and situations. Prior studies by this inventor and his colleagues have identified several important factors which may influence the performance of planting seed of several important agronomic crop species (McDaniel; McDaniel, et al.).

The present invention has the goal of improving the efficiency and speed of certain metabolic functions which occur when a seed is hydrated following planting. The more rapidly and more efficiently the metabolic processes of the seed react to environmental conditions when such conditions favor seed germination and subsequent growth, the more likely the seed can survive both biotic and environmental stresses which may inhibit growth and survival of the emerging seedling. Because perfect environmental conditions—soil composition, soil temperature, absence of soil-borne pathogens—are difficult to predict and control at planting time, any advantage which can be conferred on the seed at this time can make the difference between successful stand establishment and the necessity to replant the field, with probable attendant loss of yield and crop quality.

This invention takes advantage of the fact that added AMP (adenosine monophosphate) acts to push the equilibrium of so called "high energy" phosphates in the cells of seeds as the process of germination is initiated toward ATP (adenosine triphosphate). The greater proportion of ATP available for metabolic reactions within the cells of the germinating seed embryo is known to accelerate seed germination responses and increase resultant seedling vigor. These findings were the basis of prior art detailed in U.S. Pat. No. 4,209,316, on which the present invention is a significant and unexpected improvement.

SUMMARY

In an embodiment, a method of treating plant seed, plant seedlings, or developing plants with the chemical formulations described in the above patent along with an inhibitor or inhibitors of lipoxygenase activity, to include a catalytic amount of a magnesium salt.

In an embodiment, the treatment technique comprises applying the buffered nucleotide formulation along with an inhibitor of lipoxygenase enzyme activity, and a lesser quantity of magnesium to the surface of the seed as a dry powder mixture.

In an embodiment, the quantity of lipoxygenase enzyme inhibitor applied is from about 0.5 to about 200 mM per kilogram of seed, to include the buffered nucleotide formulation as described in the earlier referenced patent.

In another embodiment, the treatment consists the application of a lipoxygenase enzyme inhibitor plus the buffered nucleotide referenced in the earlier patent to the surface of the seed in the form of a solution or suspension in an aqueous or non-aqueous non-phytotoxic solvent.

In a particular embodiment, the concentration of lipoxygenase enzyme inhibitor in the solution or suspension applied is from $5 \times 10^{-6}$ to $2 \times 10^{-2}$ molar.

In an embodiment, the inhibitor of lipoxygenase enzyme activity is selected from the group composed of gallic acid and its C1-C8 alkyl esters.

In a particular embodiment, the inhibitor of lipoxygenase enzyme activity is chosen from the chemical group consisting of hydroxamic acid and its substituted and unsubstituted cyclic hydrocarbyl derivatives.

In an embodiment, the hydroxamic acid compound is chosen from the following group: salicylhydroxamic acid, m-toluohydroxamic acid, m-iodobenzhydroxamic acid, m-chlorobenzoic acid, 2-napthylhydroxamic acid, p-chlorobenzhydroxamic acid, benzhydroxamic acid, isonicotinylhydroxamic acid, phenyl-acetylhydroxami acid, o-carboxybenzhydroxamic acid, and cyclohexylhydroxamic acid.

In an embodiment, the inhibitor of lipoxygenase enzyme activity is chosen from a group of antioxidant compounds including: pyrocatechol, nordihydroguaiaretic acid, resorcinol, phoroglucinol, hydroquinone, coumaric acid, sinapic acid, ferulic acid, quercetin, vitamin E, butylated hydroxytoluene, butylated hydroxyanisole, linoleic acid, hydrogen peroxide, and alpha bromo-stearic acid.

In an embodiment, the method of treating seed or developing plants with one or more inhibitors of lipoxygenase activity selected from the group including propyl gallate, salicylhydroxamic acid, butylated hydroxytoluene, vitamin E, and hydroquinone in a sufficient amount to enhance seed germination and growth, when used in combination with the components of the heretofore described prior invention.

In an embodiment, the process additionally includes a concurrent treatment of the seed with a fungicide, and/or a pesticide and/or an insecticide, and/or a plant growth regulator.

In an embodiment, the concurrent chemical treatment steps occur simultaneously via treatment of the seed surface with a solution or suspension of all treatment chemicals contained in an aqueous or non-aqueous, non-phytotoxic solvent.

In an embodiment, cotton seed is treated with a buffered nucleotide formulation simultaneously with a lipoxygenase enzyme inhibitor along with a catalytic quantity of magnesium sufficient to improve growth characteristics of the seed.

In an embodiment, corn seed is treated with a buffered nucleotide formulation simultaneously with a lipoxygenase enzyme inhibitor along with a catalytic quantity of magnesium sufficient to improve growth characteristics of the seed.

In an embodiment, legume seed is treated with a buffered nucleotide formulation simultaneously with a lipoxygenase enzyme inhibitor along with a catalytic quantity of magnesium sufficient to improve growth characteristics of the seed.

In an embodiment, various oil seeds, grain seeds, and legume seeds are treated with a buffered nucleotide formulation simultaneously with a lipoxygenase enzyme inhibitor along with a catalytic quantity of magnesium sufficient to improve growth characteristics of the seed.

In an embodiment, crop seeds and developing plants are treated with a buffered nucleotide formulation simultaneously with a lipoxygenase enzyme inhibitor without the inclusion of magnesium, when soil tests confirm that added magnesium is not necessary for improved growth response of the seed or plant.

SPECIFICATION

The measure of "high energy" nucleotides in seedling tissues is the adenylate energy charge. Prior studies have confirmed the importance of available ATP in the expression of seedling vigor (McDaniel). The possibility was tested that adding an antioxidant chemical to the buffered AMP seed treatment could potentiate its action. This resulted in an unexpected salutary increase in beneficial seed germination attributes and seed vigor across several crop seed species.

Table one presents an example of the exemplary results from the application of this prior invention:

| Seed treatment | cotton lint yield in pounds/acre |
| --- | --- |
| No treatment (control) | 825 |
| Buffered AMP (liquid) | 925 (0.69 ns) |
| Buffered AMP (powder) | 1,058 (1.72*) |
| Fungicide alone | 753 |
| Buffered AMP liquid, with fungicide | 1,117 (2.11*) |

Acid delinted Pima S-5 planting cottonseed was treated with a standard formulation of buffered adenosine monophosphate (AMP), as described in U.S. Pat. No. 4,209,316. A commercial planter was utilized, and seed treatments were laid out in a randomized complete block design with eight replications in twenty foot long forty inch rows, at the Marana, Ariz. Experimental Research Station. An asterisk beside a mean indicates that a one-tailed t test shows the indicated treatment differed significantly from the control at the 95% confidence interval.

The prior invention upon which the present application technology is grounded relies upon the addition of ATP precursors, such as AMP, which are incorporated into the tissues of germinating seeds. Radioactive tracer studies confirmed this. Enzymatic conversion of these "lower energy" adenylates into ATP occurs in mitochondria of the imbibing seed. The important inclusion of an excess quantity of a non-phytotoxic buffering agent forms the basic tenet of this prior art. It is also important to maintain the pH level of the treatment chemicals within a physiological range, preferably around pH 7.0.

The significant and unexpected improvement in U.S. Pat. No. 4,209,316 which the present application describes results from the significant interaction between the mitochondrial energetic reactions and the inhibition of the ubiquitous enzyme lipoxygenase (linoleate: oxygen oxoreductase) found in the cells of almost all higher organisms, in one molecular form or another. (International Enzyme Commission No: EC 1.13.11.12) Previous research showed that the inclusion of chemical inhibitors of seed and seedling lipoxygenase activity acted to improve an array of seed properties. The result was improved seed germination rates, seed vigor and stand establishment in several crop species. Although lipoxygenase levels vary greatly across different crop species and developmental stages, overall, seed treatments with lipoxygenase inhibitors at appropriate concentrations almost invariably markedly improved seed quality characteristics (Table two). The presence of lipoxygenase isoenzymes has always been considered a necessary enzymatic constituent of seed, with the enzyme especially predominant in oil seeds. The detrimental effects of lipoxygenase activity on the viability and storage attributes of seeds have been reported by a number of authors. (Leopold; Parrish; Pfeiffer, et al.: and Hajika, et al.)

The significant improvements seen in seed quality attributes due to reduction or elimination of lipoxygenase activity by chemical inhibitors such as salicylhydroxamic acid have only rarely been noted, and then only with very toxic chemical inhibitors (Brooks, et al.). The majority of reports suggest a differential effect on seedling germination depending on temperature stress and other stresses (Ismail, et al.; Leopold, et al.). Additionally, a number of authors have reported deleterious effects of lipoxygenase activity on a variety of seed attributes, including storage deterioration and germination (Hajika, et al.; Parrish, et al.). In some instances, mitochondrial purification by density gradient centrifugation enabled the separation of alternative oxidase activity limited by lipoxygenase inhibitors from coupled oxidative phosphorylation. (Goldstein, et al.) Indeed, reduction or elimination of seed lipoxygenase activity does not appear to damage seed quality attributes or germination. (Pfeiffer, et al.). Musgrove, et al. and McDaniel have studied the possible relationship of alternative oxidation reactions affected by lipoxygenase inhibitors which may elicit the expression of male sterility in some plants. These studies serve to illustrate the broad spectrum of ways in which lipoxygenase enzymes influence plant metabolism.

Results of a small sample of such studies are illustrated in table two, where the results of seed treatments using the preferred lipoxygenase inhibitor propyl gallate alone are presented. Propyl gallate is the inhibitor and antioxidant of choice for inclusion in the improvement of U.S. Pat. No. 4,209,316 described in this application. Hydroquinone, another lipoxygenase inhibitor, was also effective. Data presented are a representative excerpt from a much larger multilocation replicated set of field plots comparing two lipoxygenase inhibitors. Selected location: Safford, Arizona Experimental Research Station. Each data entry represents the mean of replicated random samples plus or minus the standard error. The smaller the emergence coefficient, the faster the speed of seedling emergence from the soil. All treatments except the first control received a fungicide co-treatment. Lipoxygenase inhibitors were coated on the seed at a rate of 2.0 grams per kilogram of dry seed.

Table two presents these results:

| Treatment | Germination % | Surviving Stand % | Seedling Ht. (cm) | Emergence Coeff. |
|---|---|---|---|---|
| Control | 18.4 ± 2.0 | 54.0 ± 3.6 | 14.7 ± 0.7 | 0.57 ± 0.04 |
| Control (with *fungicide*) | 21.7 ± 3.2 | 60.4 ± 2.8 | 15.3 ± 0.7 | 0.50 ± 0.03 |
| Propyl Gallate (with *fungicide*) | 23.0 ± 2.3 | 57.8 ± 3.0 | 17.3 ± 0.6 | 0.52 ± 0.03 |
| Hydroquinone (with *fungicide*) | 22.9 ± 3.1 | 60.6 ± 3.5 | 16.6 ± 0.4 | 0.50 ± 0.04 |

These data suggest that lipoxygenase activity is a significant oxygen competitor during the initial stages of seed germination. The oxygen necessary to initiate, fuel, and sustain cellular respiration and mitochondrial energy conservation via oxidative phosphorylation enters the seed as germination begins. It is then partially diverted to catalyze lipoxygenase oxygenation. As a consequence, ATP bond energy will be insufficient to optimize and maximize an acceleration of germination processes leading to autotrophic plant development. The inhibition of seed lipoxygenase activity, therefore acts to significantly improve both the speed and vigor which the developing seedling can express.

One might reason that antioxidant activity would be an important component of lipoxygenase inhibitor action, as presence of a considerable quantity of oxygen radicals would be present during initial seed respiratory processes. When much higher concentrations of several classical antioxidants, including ascorbic acid, vitamin E, and butylated hydroxylated toluene were applied to seeds, no enhancement of seed germination and viability traits were observed. Positive results would have supported a significant role for an antioxidant mechanism in the seed improvements reported in the present application.

Most surprising, experiments designed to test the effects of adenosine monophosphate seed treatments in combination with co-treatments of lipoxygenase inhibitors resulted in salutary improvements in a number of crop seed and seedling attributes. If this hypothesis were correct it might be expected that inclusion of a lipoxygenase enzyme inhibitor as a seed treatment component would lead to improved planting seed performance in oilseeds, which are known to contain high levels of various lipoxygenase isozymes. As lipoxygenases are associated with seed quality deterioration across a number of oilseeds, including soybeans, it is reasonable to consider that inhibition could result in giving the seed the ability to resist deterioration over time. This could enable a seed to maintain a higher germination rate and vigor level for a longer storage time.

Unexpectedly, crop species with high lipoxygenase activity, like soybean, or grain crops, like corn, which exhibit lower levels of lipoxygenase activity when treated with the buffered AMP formulation along with a chemical lipoxygenase inhibitor, showed significant improvements in seed germination rate, seedling vigor, and stand establishment, and when carried through to harvest, in crop yields. Table three illustrates the comparative advantage of the combination of buffered AMP and propyl gallate liquid formulation applied to two sets of Acala type cottons container grown in Tucson, Ariz. An extended harvest period was possible. Seed cotton was hand picked over several weeks. Bolls with fiber and seed were dried, individually weighed, and treatments were separated and bulked together. Osmocote complete fertilizer was applied twice—at two and four weeks—following the chemical formulation applications.

Table three gives the results:

| | Combined weight of harvested seed cotton per group (in grams) | |
|---|---|---|
| Treatment: | group one | group two |
| Control | 384 | 432 |
| Propyl Gallate | 640 | 423 |
| Buffered AMP and Propyl Gallate | 708 | 576 |

The fourth example of the advantages of the combination of buffered AMP along with propyl gallate compares the stalk diameter of a field grown corn cultivar (Pioneer 1365) with the same cultivar treated with only buffered AMP. Commercial corn planting seeds were treated in the "hopper box" with a typical liquid formulation of the treatments (pre-mixed with the seed in a small rotary mixer). Additionally, the buffered AMP plus propyl gallate included a minor amount of magnesium sulfate (about one tenth the quantity of propyl gallate by weight). In example four, corn stalk diameter measurements were made just above the lower prop roots and again about ten centimeters higher. Average stalk diameters were 5.5 and 6.0 cm for the buffered AMP treatment and 7.0 and 7.0 cm for the combination treatment of both buffered AMP and propyl gallate, along with magnesium sulfate. These formulations have been successfully evaluated this season in commercial corn production areas.

Such dramatic improvements in planting seed performance also are especially important commercially because the nucleotide treatments which form the basis of U.S. Pat. No. 4,209,316 along with the non-toxic buffers included, are naturally occurring components of nearly all living eukaryotic cells. As such, no toxic or negative effects would be expected to result from treatment of seed or young plants at the seedling stage with these formulations. Additionally, lipoxygenase inhibitors, in the preferred embodiment presented in this application, consisting of propyl gallate, which often is included as a food additive, and which appears on the GRAS list (generally recognized as safe), also serve to make the seed treatments described here extremely environmentally benign. As phosphate buffers utilized are localized to the immediate surrounding of the seed, or even when applied as a layby treatment by the seed row, the quantity of phosphate utilized would be insignificant in relation to normal fertility practices.

A role for magnesium as a critical plant micronutrient has been reported in a number of agricultural field areas in the southwest. Specifically in Arizona soils, studies by Smith et al. have shown a need for magnesium supplementation for crops such as alfalfa. Previous work by myself and my colleagues, (McDaniel, et al.), have demonstrated the importance of magnesium as a necessary component of reaction mixtures used to support the coupled oxidative phosphorylation and respiration of mitochondria isolated from the cells of germinating seedlings of a number of crops. Evidence points to the presence of magnesium ion as a necessary element in the potentiation of mitochondrial ATP production. This in turn suggests an important role for magnesium in helping the cells of the plant embryo synthesize the necessary ATP to promote rapid germination.

The importance of magnesium as a component in the formulation of plant tissue culture media, as well as its usual inclusion in microfertilizers and specialty fertilizers is well known. This application does not consider addition of magnesium sulfate or magnesium chloride in non-chelated form as an absolute requirement for the practice of the present invention. This is due to the difficulty in adequately testing for a significant effect of magnesium when added to AMP and propyl gallate formulations in field tests. Population densities of soil flora and fauna, as well as concentrations and potential availability of soil minerals, are in constant flux. This makes accurate measurements in the field over time extremely difficult. However, the data support the addition of "catalytic" amounts of magnesium to the growth-promoting chemical formulations specified in this application, if soil proves to be depauperate in magnesium, or if field areas which have been fallow for extended periods of time are within known areas of low magnesium content.

What is claimed is:

1. A composition for the treatment of seeds and plants comprising adenosine monophosphate, a non-phytotoxic buffer, 0.005 mM to 20 mM of propyl gallate and a catalytic quantity of magnesium.

2. The composition of claim 1 wherein the composition is in a form selected from the group consisting of a solution in an aqueous non-phytotoxic solvent, a solution in a non-aqueous non-phytotoxic solvent, a suspension in an aqueous non-phytotoxic solvent, and a suspension in a non-aqueous non-phytotoxic solvent aqueous non-phytotoxic solvent.

3. The composition of claim 1, further comprising one or more inhibitors of lipoxygenase activity selected from the group consisting of gallic acid, gallic acid methyl ester, gallic acid ethyl ester, gallic acid butyl ester, gallic acid pentyl ester, gallic acid hexyl ester, gallic acid heptyl ester and gallic acid octyl ester.

4. The composition of claim 1, further comprising one or more inhibitors of lipoxygenase activity selected from the group consisting of hydroxamic acid, salicylhydroxamic acid, m-toluohydroxamic acid, m-iodobenzhydroxamic acid, m-chlorobenzoic acid, 2-naphthylhydroxamic acid, p-chlorobenzhydroxamic acid, benzhydroxamic acid, isonicotinylhydroxamic acid, phenylacetylhydroxamic acid, o-carboxybenzhydroxamic acid and cyclohexylhydroxamic acid.

5. The composition of claim 1, further comprising one or more inhibitors of lipoxygenase activity selected from the group consisting of pyrocatechol, nordihydroguaiaretic acid, resorcinol, phloroglucinol, hydroquinone, coumaric acid, sinapic acid, ferulic acid, quercetin, vitamin E, butylated hydroxytoluene, butylated hydroxyanisole, linoleic acid, hydrogen peroxide and alpha-bromostearic acid.

6. The composition of claim 1, further comprising one or more inhibitors of lipoxygenase activity selected from the group consisting of salicylhydroxamic acid, butylated hydroxytoluene, vitamin E and hydroquinone.

7. The composition of claim 6, further comprising one or more compounds selected from the group consisting of fungicide, pesticide, insecticide and plant growth regulator.

8. The composition of claim 1, wherein the composition is a dry powder mixture.

* * * * *